US008940796B2

(12) United States Patent
Bubnis et al.

(10) Patent No.: US 8,940,796 B2
(45) Date of Patent: Jan. 27, 2015

(54) PHENYLEPHRINE LIQUID FORMULATIONS

(75) Inventors: William Bubnis, Mechanicsville, VA (US); Stephanie Shield, Richmond, VA (US); Amanda Alley, Midlothian, VA (US)

(73) Assignee: Wyeth LLC, New York, NY (US)

( * ) Notice: Subject to any disclaimer, the term of this patent is extended or adjusted under 35 U.S.C. 154(b) by 1297 days.

(21) Appl. No.: 11/704,407

(22) Filed: Feb. 9, 2007

(65) Prior Publication Data

US 2007/0197661 A1 Aug. 23, 2007

Related U.S. Application Data

(60) Provisional application No. 60/774,634, filed on Feb. 21, 2006.

(51) Int. Cl.
*A01N 33/24* (2006.01)
*A61K 31/13* (2006.01)
*A01N 33/02* (2006.01)
*A61K 31/135* (2006.01)

(52) U.S. Cl.
USPC .......................................... 514/653; 514/649

(58) Field of Classification Search
USPC ....................................................... 514/653
See application file for complete search history.

(56) References Cited

U.S. PATENT DOCUMENTS

| 3,515,781 | A | 6/1970 | Steinberg et al. |
| 5,405,604 | A * | 4/1995 | Hall ................................. 424/54 |
| 5,616,621 | A | 4/1997 | Popli et al. |
| 5,730,997 | A | 3/1998 | Lienhop et al. |
| 5,759,579 | A | 6/1998 | Singh et al. |
| 6,462,094 | B1 * | 10/2002 | Dang et al. ...................... 514/25 |
| 6,509,492 | B1 | 1/2003 | Venkataraman |
| 2003/0060422 | A1 | 3/2003 | Venkataraman |
| 2004/0234457 | A1 * | 11/2004 | Rennie et al. ................... 424/46 |
| 2005/0266031 | A1 * | 12/2005 | Dickerson et al. ............. 424/400 |
| 2006/0121066 | A1 * | 6/2006 | Jaeger et al. .................. 424/400 |
| 2007/0160689 | A1 | 7/2007 | Giordano et al. |
| 2008/0234291 | A1 * | 9/2008 | Francois et al. ......... 514/254.07 |

FOREIGN PATENT DOCUMENTS

| EP | 0 559 463 A1 | 9/1993 |
| WO | 2006/064327 A1 | 6/2006 |
| WO | WO 2007/143156 A1 | 12/2007 |

* cited by examiner

*Primary Examiner* — Layla Soroush
(74) *Attorney, Agent, or Firm* — Joseph F. Reidy; Jeff Gold

(57) ABSTRACT

An oral, aqueous-based, liquid pharmaceutical composition is provided. The composition comprises up to about 45% w/v glycerin and up to about 10% w/v sorbitol wherein the glycerin to sorbitol ratio is about 2:1 to 10:1.

21 Claims, No Drawings

PHENYLEPHRINE LIQUID FORMULATIONS

This application claims priority from U.S. Provisional Application file 60/774,634 filed on Feb. 21, 2006 entitled "Phenylephrine Liquid Formulations", the content of which is incorporated herein in its entirety to the extent that it is consistent with this invention and application.

FIELD OF THE INVENTION

An aqueous, oral liquid pharmaceutical composition comprising phenylephrine is provided. The composition is particularly well suited for the relief of cold, cough, flu, fever, headache, pain, body ache, migraine and allergy symptoms in pediatric patients.

BACKGROUND OF THE INVENTION

Orally administered pharmaceutical compositions are provided to patients in many dosage forms, including solid forms such as capsules, caplets or tablets and liquid forms such as solutions and suspensions. For many patients including young children, older persons and incapacitated persons, a liquid dose form is preferable because of the ease with which it may be swallowed.

Many liquid cough and cold compositions contain large amounts of sorbitol and other sugars, typically included to improve palatability. For example, U.S. Pat. No. 5,730,997 discloses a composition containing about 20% to about 45% by weight sorbitol and about 10% to about 15% by weight hydrogenated maltose syrup. Such compositions are purported to improve palatability but high levels of sorbitol and maltose may contribute to the degradation of active ingredients such as phenylephrine, for example.

Accordingly, it would be desirable to have a palatable, liquid dosage form comprising phenylephrine with reduced propensity for degradation of phenylephrine.

SUMMARY OF THE INVENTION

The pharmaceutical described herein is an aqueous oral pharmaceutical composition comprising phenylephrine, artificial sweetener, up to about 45% w/v glycerin and up to about 10% w/v sorbitol wherein the glycerin to sorbitol ratio is about 2:1 to about 10:1.

The composition may further comprise one or more second active agents selected from analgesics, decongestants, expectorants, anti-tussives, antipyretics, anti-inflammatory agents, cough suppressants and antihistamines.

The composition may be a solution or a suspension. Suspension embodiments may further comprise viscosity modifying agents.

DETAILED DESCRIPTION OF THE INVENTION

The invention provides an oral, aqueous-based, liquid pharmaceutical composition comprising the pharmaceutical active phenylephrine. The composition is palatable and has improved phenylephrine stability. The composition comprises phenylephrine, an artificial sweetener, up to about 45% w/v glycerin and up to about 10% w/v sorbitol. The glycerin to sorbitol ratio is about 2:1 to about 10:1. The inventors believe, without wishing to be bound to the theory, that the glycerin to sorbitol ratio is beneficial to both maintaining desirable organoleptic properties and reducing the opportunity for phenylephrine degradation. The composition of the invention may be a solution or a suspension.

Preferably the phenylephrine is in a salt form. Suitable salt forms include, but are not limited to, phenylephrine hydrochloride (HCl), hydrobromide (HBr), bitartarate and tannate salts. Phenylephrine may be used in an amount of about 0.001% w/v to about 10% w/v. Preferably, phenylephrine is used in an amount of about 0.005% w/v to about 2.5% w/v. Herein % w/v means a percentage determined by the following formula:

$$w/v\ \% = \frac{\text{Weight of component (in grams)}}{\text{Volume of composition (in milliliters)}} \times 100 \quad (1)$$

Accordingly, for example, 1% w/v % phenylephrine means 1 gram of phenylephrine in 100 ml of the oral liquid composition.

An artificial sweetener is provided to improve palatability. An artificial sweetener is preferred for use as a sweetener to the use of conventional sugar sweeteners as the inventors believe, without wishing to be held to the theory, that conventional sugars may contribute to the degradation of phenylephrine in aqueous based compositions. Suitable artificial sweeteners, include but are not limited to sucralose, saccharine salts, cyclamates, acesulfame K, dipeptide based sweeteners, aspartame and mixtures thereof. Sucralose, which is a high intensity sweetener, is particularly well suited for use in the composition. Sucralose may be used in an amount of about 0.01% w/v to about 0.4% w/v, for example. The appropriate amount of artificial sweetener depends on properties and sweetness intensity of the artificial sweetener and target organoleptic properties of the composition. One skilled in the art is familiar with the characteristics of sweeteners and methods for determining amount of sweetener to be used.

Glycerin and sorbitol are used in the composition. In contrast to many conventional commercial cold products, the composition contains more glycerin than sorbitol. The inventors believe, without wishing to be bound to the theory, that reduced amounts of sorbitol facilitate stability of the phenylephrine and that the glycerol to sorbitol ratio is important in achieving a stable, palatable composition. The composition may contain up to 45% w/v glycerin and up to about 10% w/v sorbitol. More preferably the composition may contain about 18% to about 30% w/v glycerin and about 3% to about 10% w/v sorbitol. Herein the amounts of sorbitol and glycerin are the amounts of standard commercial preparations of sorbitol and glycerin. Commercial sorbitol (as obtained from SPI Polyols, 321 Cherry Lane New Castle, Del. 19720, or Roquelte Frèves 62080 Lestrew, France, for example) is an aqueous based composition which is 70% sorbitol. Commercial glycerin (as obtained from Dow Chemical Co., 2030 Dow Center, Midland, Mich. 48674, or Lyondell, 1221 McKinney St., Houston, Tex. 77253, for example) is 96% glycerin. One skilled in the art is familiar with these commercial preparations and methods of adjusting amounts should a different glycerin or sorbitol preparation be used.

The composition may contain one or more additional pharmaceutical actives (also referred to as "active(s)", "active agent(s)", "therapeutic agent(s)", "drug(s)"). Herein reference to "first pharmaceutical active" means phenylephrine and reference to "second pharmaceutical active" means any active other than phenylephrine. Further, the term second pharmaceutical active may refer to a single species of active or a plurality of species of actives other than phenylephrine (e.g., the total number of actives in the compositions may be greater than 2.) For embodiments of the composition which are solutions, any additional active should be water soluble. A water-soluble pharmaceutical active means a pharmaceutical active indicated to be soluble in water by the Merck Index. Additional actives in suspension embodiments may be water soluble, slightly soluble in water, or insoluble in an aqueous medium. It should be noted that second pharmaceutical actives are discussed herein in the context of compositions comprising phenylephrine, but aqueous based compositions having the sorbitol and glycerin ratios discussed herein may be likewise suitable for compositions comprising one or more of the second active agents in the absence of phenylephrine.

Suitable additional or second active agents include analgesics, decongestants, expectorants, anti-tussives, antipyretics, anti-inflammatory agents, cough suppressants and antihistamines.

Antihistamines useful in the practice of the present invention (along with their preferred salt form) include, but are not limited to, chlorpheniramine (maleate), brompheniramine (maleate); dexchlorpheniramine (maleate), dexbrompheniramine (maleate), triprolidine (HCl), diphenhydramine (HCl, citrate), doxylamine (succinate), tripelenamine (HCl), cyroheptatine (HCl), chlorcyclizine (HCl), bromodiphenhydramine (HCl), phenindamine (tartrate), pyrilamine (maleate, tannate), azatadine (maleate); acrivastine, astemizole, azelastine, cetirizine, ebastine, fexofenadine, ketotifen, carbinoxamine (maleate), desloratadine, loratadine, pheniramine maleate, thonzylamine (HCl), mizolastine and terfenadine.

Antitussives useful in the practice of the present invention (along with their preferred salt form) include, but are not limited to, chlophendianol, caramiphen (ediylate), dextromethorphan (HBr), diphenhydramine (citrate, HCl, codeine (phosphate, sulfate) and hydrocodone.

Decongestants useful in the practice of the invention (along with their preferred salt form) include, but are not limited to, pseudoephedrine (HCl, sulfate), Ephedrine (HCl, Sulfate), phenylephrine (bitartarate, tannate, HBr, HCl), and phenyl-propenolamine (HCl).

Expectorants which may be used in the practice of the invention (along with their preferred salt form) include but are not limited to terpin hydrate, guaifenesin (glycerol, guaiacolate), potassium (iodide, citrate) and potassium guaicolsulfonate.

Non-steroidal anti-inflammatory drugs (NSAIDS) which may be used in the practice of the invention include, but are not limited to, propionic acid derivatives such as ibuprofen, naproxen, ketoprofen, flurbiprofen, fenoprofen, suprofen, fluprofen and fenbufen; acetic acid derivatives such as tolmetin sodium, zomepirac, sulindac, and indomethacin; fenamic acid derivatives such as mefenamic acid and meclofenamate sodium; biphenyl carboxylic acid derivatives such as diflunisal and flufenisal and oxicams such as piroxicam, sudoxicam and isoxicam.

Cox 2 inhibitors which may be used in the practice of the invention include, but are not limited to, Celecoxib, Rofecoxib and Valdecoxib.

Analgesics which may be used in the practice of the invention include but are not limited to aspirin, acetominophen, phenacetin and salicylate salts.

Examples of substantially insoluble pharmaceutical actives that may be suspended in the suspending system of suspension embodiments include, but are not limited to, nabumetone, glimepiride, diclofenac, piroxicam and meloxican.

Of the pharmaceutically active compounds described above which may be included in addition to phenylepherine in the composition, those which are particularly preferred are set forth below along with preferred ranges for their inclusion into the claimed pharmaceutical composition.

Chlorpheniramine may be used in the pharmaceutical composition in amounts between about 0.01 w/v and about 0.05 w/v. Preferably chlorpheniramine, when used in the pharmaceutical composition, is present in the amount of about 0.01 w/v to 0.03 w/v.

Brompheniramine maleate may be used in the pharmaceutical composition, preferably in the amount of about 0.01 w/v to about 0.03 w/v.

Dextromethorphan HBr may be used in the pharmaceutical composition, preferably in the amount of about 0.05 w/v to about 0.250 w/v.

Guaifenesin may be used in the composition in amounts of about 0.4% w/v to about 6% w/v and preferably in amounts of about 2% w/v to about 4% w/v.

Acetaminophen may be used in the composition in amounts of about 0.2% w/v to about 10% w/v and preferably in amounts of about 0.5% w/v to about 3.2% w/v.

Chlophendianol may be used in the composition in amounts of about 0.1% w/v to about 1% w/v and preferably in amounts of about 0.25% w/v to about 0.5% w/v.

Diphenhydramine may be used in the composition in amounts of about 0.2% w/v to about 2% w/v and preferably in amounts of about 0.5% w/v to about 1% w/v.

Brompheniramine may be used in the composition in amounts of about 0.016% w/v to about 0.16% w/v and preferably in amounts of about 0.02% w/v to about 0.08% w/v.

Loratadine may be used in the composition in amounts of about 0.02% w/v to about 0.4% w/v and preferably in amounts of about 0.1% w/v to about 0.2% w/v.

Aspirin may be used in the composition in amounts of about 0.8% w/v to about 13% w/v and preferably in amounts of about 3.2% w/v to about 7.2% w/v.

Doxylamine may be used in the composition in amounts of about 0.1% w/v to about 1% w/v and preferably in amounts about 0.25% w/v to about 0.5% w/v.

Amounts of pharmaceutically active compounds incorporated are conventional dosages known to those skilled in the art. Further, for pharmaceutical compositions intended for use in the United States, amounts of pharmaceutical actives are preferably in compliance with applicable FDA regulations regarding dosage of such compounds.

The pharmaceutically active compounds are preferably of N.F. (National Formulary) or U.S.P. (United States Pharmacopeia) grade.

Excipients known by those skilled in the art may be useful in the practice of the present invention. Such excipients may include, but are not limited to, humectants such as propylene glycol, defoaming agents, buffers, electrolytes, preservatives such as sodium benzoate and disodium edetate, antioxidants, taste masking agents and various flavoring and coloring agents, for example.

Examples of suitable flavoring agents include, but are not limited to, natural and artificial flavors such as mints (i.e., peppermint, etc.), menthol, chocolate, artificial chocolate, bubblegum, both artificial and natural fruit flavors (i.e., cherry, grape, orange, strawberry, etc.) and combinations of two or more thereof. It is preferable to avoid flavoring agents which have aldehyde functional groups (e.g. use non-aldehyde containing flavorants is preferred). Flavoring agents are generally provided as a minor component of the composition in amounts effective to provide palatable flavor to the compositions. Typically, flavoring agents are present in amounts in the range of about 0 grams to about 5 grams per 100 ml of the composition.

Preservatives useful in the present invention include but are not limited to sodium benzoate, sorbates, such as potassium sorbate, salts of edetate (also known as salts of ethylenediaminetetraacetic acid or EDTA, such as disodium edetate), benzaldionium chloride and parabens (such as methyl, ethyl, propyl, and butyl p-hydroxybenzoic acid esters). Preservatives listed above are exemplary, but each preservative must be evaluated on an experimental basis, in each formulation to assure compatibility and efficacy of the preservative. Methods for evaluating the efficacy of preservatives in pharmaceutical formulations are known to those skilled in the art. Sodium benzoate and disodium edetate are the presently preferred preservative ingredients.

Preservatives are generally present in amounts of up to one gram per 100 ml of the pharmaceutical composition. Preferably the preservatives are present in amounts in the range of from about 0.01 w/v to about 0.4 w/v of the composition. Typically, the preservative sodium benzoate would be present in the range of about 0.1 w/v to about 0.2 w/v of the composition, for example. Sodium benzoate was used in a concentration of about 0.1 w/v in an exemplary embodiment of the composition.

Propylgallate is exemplary of an antioxidant that is suitable for use in the composition.

Sodium citrate is exemplary of a buffering agent which may be used in the composition. It is preferable to buffer the composition to maintain the pH less than about 5.4. More preferably the pH may be maintained in the range of about pH 2 to about pH 4.5.

Coloring agents may also be incorporated in the pharmaceutical composition to provide an appealing color to the composition. The coloring agents should be selected to avoid chemical incompatibilities with other ingredients in the composition. Suitable coloring agents are well known to those skilled in the art.

In some embodiments, particularly suspension embodiments, a surface-modifying agent, such as a surfactant, may be used in the pharmaceutical composition to modify the surface of the suspended components. Such surface modification is believed to facilitate diminished irreversible aggregation of the suspended particles. The surfactant may be an ionic or non-ionic surfactant or mixtures thereof. Exemplary surfactants include but are not limited to polysorbates (tweens), Spans™, togats, lecithin, polyoxyethylene-polyoxypropylene block copolymers and medium chain mono/diglycerides.

Typically, suspension embodiments will further comprise a viscosity modifying agents. Suitable viscosity modifying agents include but are not limited to chitosan, xanthan, hydroxypropylmethylcellulose (HPMC), hydroxypropylcellulose (HPC), hydroxyethylcellulose (HEC), glactomannons such as guar, konjac, locust bean gum and mamman, for example, microcrystalline cellulose and combinations thereof.

Xanthan gums suitable for use in the present invention are high molecular weight polysaccharides such as the xanthan gum produced by *Xanthamonas capestris*, for example. Xanthan gum is an article of commerce and is available, for example, from manufacturers such as: Rhodia, Inc. under the brand name Rhodigel™ and from Kelco™, a division of Merck. Rhodigel™ 80 Pharm Grade is exemplary of one specific commercial product suitable for use in the practice of the invention.

Microcrystalline cellulose is commercially available from suppliers such as FMC (1735 Market Street, Philadelphia, Pa. 19103) under the tradename Avicel™

The amount of viscosity modifier used depends on the desired "thickness" of the composition and the type viscosity modifier used. Combinations of viscosity modifiers may be employed. For example, in an exemplary embodiment with a viscosity of about 1500 to about 4500 cps, up to about 1.0 w/v xanthan gum may be used with up to about 3.0 w/v microcrystalline cellulose may be as a viscosity modifier.

It is preferable to avoid viscosity modifiers with a significant presence of negatively charged moieties or moieties with propensity to ionize to a negative charge if the structure of the modifier is such that the negatively charged moiety is readily available for reaction.

Suspensions are useful for preparing compositions comprising actives that are substantially insoluble in water. In suspension embodiments the phenylephrine is dissolved in the aqueous medium. The composition may contain one or more second active agents dissolved in the aqueous medium and/or one or more substantially water insoluble second active agents may be suspended in the composition. For the suspension embodiments, it is preferable that both the suspended substantially insoluble active ingredients and any soluble active ingredients dissolved in the aqueous medium, are distributed to form a substantially homogeneous distribution of active ingredients in the pharmaceutical composition.

Exemplary pharmaceutical actives that are substantially insoluble in the aqueous composition and would be expected to form suspension include but are not limited to Ibuprofen, Ketoprofen, Naproxen, Celecoxib, Rofecoxib, Valdecoxib, Nabumetone, Glimepiride, Diclofenac, Piroxicam and Meloxican. For pharmaceutical actives not specified on this list a pharmaceutical active substantially insoluble in the aqueous composition means a pharmaceutical active designated as relatively insoluble or insoluble in water by the Merck Index.

Typically, the composition is provided to a patient in need of treatment in a dosage unit of 5 ml although other dosage units may be likewise suitable. The dosage unit may be provided as a single dosage unit or multiples thereof, based on age, weight and other health parameters determined by a physician to be relevant.

Example 1

An exemplary composition comprising the single first pharmaceutical active phenylephrine is provided in Table 1. This composition is representative and one of many composition that are within the scope of the invention. The exemplary embodiment is provided for illustrative purposes.

TABLE 1

| Ingredient | Amount (grams/100 ml × 100) |
|---|---|
| Phenylephrine HCl | 0.05% w/v |
| Glycerin (96% USP) | 25% w/v |
| Sorbitol (70% Solution USP) | 10% w/v |
| Citric Acid | 0.75% w/v |
| Micronized Sucralose Powder (NF) | 0.2% w/v |
| menthol | 0.02% w/v |
| propylene glycol | 1.3% w/v |
| colorant | 0.01% w/v |
| sodium citrate | 0.15% w/v |
| sodium benzoate | 0.1% w/v |
| purified $H_2O$ USP | sufficient quantity to make final volume |

The composition of Table 1 may be prepared by simple mixing. The ingredients are mixed in a vessel equipped with a mechanical stirrer (e.g., a lightnin mixer), the vessel is calibrated and marked to designate the final volume. An aliquot of water substantially less than the target final volume is placed in the vessel and the other ingredient are added sequentially with mixing. Colorants are premixed with a small amount of water prior to addition to the main. Likewise, menthol and propylene glycol, are premixed before addition to the main vessel. After all other ingredients have been added and mixed sufficiently to dissolve, water is added to bring the total volume of the composition to the predetermined final volume and mixing was continued for approximately 10 minutes.

Example 2

An exemplary composition comprising phenylephrine and a second active Brompheniramine maleate is provided in Table 2. This composition is representative and one of the many compositions that are within the scope of the invention. The exemplary embodiment is provided for illustrative purposes.

TABLE 2

| Ingredient | Amount (grams/100 ml + 100) |
|---|---|
| Phenylephrine HCl | 0.05% w/v |
| Brompheniramine Maleate | 0.02% w/v |
| Glycerin (96% USP) | 25% w/v |
| Sorbitol (70% Solution USP) | 10% w/v |
| Citric Acid | 0.75% w/v |
| Micronized Sucralose | 0.2% w/v |
| Artificial Fruit Flavor | 0.2% w/v |
| Colorant | <0.1% w/v |
| Sodium Citrate | 0.10% w/v |
| Sodium Benzoate | 0.1% w/v |
| Purified H$_2$O | Sufficient quantity to make final volume |

The composition of Table 2 may be prepared using the manner of preparation described in Example 1.

Example 3

Stability data for compositions comprising phenylephrine are provided in Tables 3 and 4. Compositions comprising 0.05% w/v of phenylephrine in an aqueous based composition using the conventional commercial proportions of 25% w/v to 40% w/v sorbitol and the composition of one embodiment of the invention comprising 0.05% w/v phenylephrine in an aqueous based composition using the proportion of 25% glycerin to 10% sorbitol were prepared and subjected to stability testing. The compositions were alike in all other respects except the glycerin to sorbitol ratio.

Table 3 shows the results of stability testing over one month at conditions of 60° C. and 60% relative humidity (herein "60/60"). Table 4 shows the results of stability testing over six months at conditions of 40° C. and 75% relative humidity (herein "40/75"). For both Table 3 and 4, stability was assessed as the amount of phenylephrine degradants present as compared to amount of phenylephrine at the indicated time point. At the indicated time points, samples of the composition were analyzed by HPLC (high pressure liquid chromatography) and the total peak area attributed to phenylephrine degradants was compared to the peak area of Phenylephrine. Accordingly, the percentages reported in Tables 3 and 5 are percentages based on the total peak area of all phenylephrine degradants to the peak area of phenylephrine for the sample analyzed.

TABLE 3

| Time (months) | Phenylephrine Degradants Gly:Sorb 25:48 | Phenylephrine Degradants Gly:Sorb 25:10 |
|---|---|---|
| 0 | 0.07 | 0 |
| 0.25 | 0.26 | 0 |
| 0.5 | 0.72 | 0 |
| 1 | 1.37 | .029 |

TABLE 4

| Time (months) | Phenylephrine Degradants Gly:Sorb 25:48 | Phenylephrine Degradants Gly:Sorb 25:10 |
|---|---|---|
| 0 | 0.07 | 0 |
| 1 | 0.08 | 0 |
| 2 | 0.16 | 0 |
| 3 | 0.12 | 0 |
| 6 | 0.4 | 0 |

As Table 3 shows under conditions of 60/60 no phenylephrine degradants were detected in the composition of the invention for the first three weeks of the study and only 0.29% phenylephrine degradants were detected at the end of the fourth week of the study. In contrast phenylephrine degradants were observed at every test point for the conventional composition with 1.37% phenylephrine degradants detected at the end of the fourth week of the study.

As Table 4 shows, under conditions of 40/75, no phenylephrine degradants were observed over the six-month course of the study for the composition of the invention. In contrast phenylephrine degradants were observed at every test point for the conventional composition with 0.4% phenylephrine degradants at the end of the sixth month of the study.

Although the foregoing invention has been described in some detail by way of illustrations and examples for purposes of clarity of understanding. It will be obvious that certain changes and modifications may be practiced within the scope of the appended claims. Modifications of the above-described modes of practicing the invention that are obvious to persons of skill in the art are intended to be included within the scope of the following claims.

What is claimed is:

1. An aqueous oral pharmaceutical composition comprising:
   a). 0.05% w/v phenylephrine;
   b). 0.2% w/v sucralose;
   c). 25% w/v glycerin;
   d). 10% w/v sorbitol wherein the glycerin to sorbitol ratio is 2.5 to 1; and
   e.) wherein the composition is substantially free of phenylephrine degradants as measured under conditions of 60° C. and 60% relative humidity for approximately three weeks.

2. The composition of claim 1, further comprising a flavor system.

3. The composition of claim 2, wherein the flavor system includes non-aldehyde flavorants.

4. The composition of claim 1, further comprising at least one second active agent selected from the group consisting of analgesics, decongestants, expectorants, antitussives, antipyretics, anti-inflammatory agents, cough suppressants and antihistamines.

5. The composition of claim 4, wherein the second active agent is selected from the group consisting of non-steroidal anti-inflammatory drugs (NSAIDS), propionic acid derivatives, ibuprofen, naproxen, ketoprofen, flurbiprofen, fenoprofen, suprofen, fluprofen, fenbufen; acetic acid derivatives, tolmetin sodium, zomepirac, sulindac, indomethacin, fenamic acid derivatives, mefenamic acid meclofenamate sodium, biphenyl carboxylic acid derivatives, diflunisal, flufenisal, oxicams, piroxicam, sudoxicam, isoxicam, chlorpheniramine, brompheniramine; dexchlorpheniramine, dexbrompheniramine, triprolidine, chlorcyclizine, diphenhydramine, doxylamine, tripelenamine, cyproheptatine, bromodiphenhydramine, phenindamine, pyrilamine, azatadine, acrivastine, astemizole, azelastine, cetirizine, ebastine, fexofenadine, ketotifen, carbinoxamine, desloratadine, loratadine, pheniramine, thonzylamine, mizolastine, terfenadine, chlophendianol, caramiphen, dextromethorphan, diphenhydramine, codeine, hydrocodone, pseudoephedrine, ephedrine, phenylephrine, phenylpropenolamine, terpin hydrate, guaifenesin, potassium, potassium guaicolsulfonate, Cox 2 inhibitors, Celecoxib, Rofecoxib, Valdecoxib, aspirin, acetaminophen, phenacetin, salicylate salts and combination thereof.

6. The composition of claim 4, wherein the at least one second active agent is selected from the group consisting of chlorpheniramine, dextromethorphan, guaifenesin, acetaminophen, chlophendianol, diphenhydramine, brompheniramine, loratadine, aspirin and doxylamine succinate.

7. The composition of claim 1, further comprising a buffering agent.

8. The composition of claim 7, wherein the buffering agent maintains a pH below about 5.4 in the composition.

9. The composition of claim 7, wherein the buffering agent maintains a pH between about 2 and about 4.5 in the composition.

10. The composition of claim 1, further comprising a preservative.

11. The composition of claim 10, wherein the preservative is selected from the group consisting of sodium benzoate, sorbates, parabens, EDTA and combinations thereof.

12. The composition of claim 1, further comprising an antioxidant.

13. The composition of claim 12, wherein the antioxidant is propyl gallate.

14. An aqueous pharmaceutical solution comprising:
 a). 0.05% w/v phenylephrine;
 b). 0.2% w/v sucralose;
 c). 25% w/v glycerin;
 d). 10% w/v sorbitol, wherein the glycerin to sorbitol ratio is 2.5:1;
 e). 0.02% w/v brompheniramine; and
 f.) wherein the composition is substantially free of phenylephrine degradants as measured under conditions of 60° C. and 60% relative humidity for approximately three weeks.

15. The solution of claim 14, further comprising up to about 1.25% w/v citric acid.

16. The solution of claim 14, further comprising up to about 0.2% w/v propyl gallate.

17. An aqueous oral pharmaceutical suspension composition comprising:
 a). 0.05% w/v phenylephrine,
 b). 0.2% w/v sucralose,
 c) a viscosity modifying agent,
 d). 25% w/v glycerin,
 e). 10% w/v sorbitol wherein the glycerin to sorbitol ratio is 2.5:1; and
 f.) wherein the composition is substantially free of phenylephrine degradants as measured under conditions of 60° C. and 60% relative humidity for approximately three weeks.

18. The suspension of claim 17, wherein the viscosity modifying agent is selected from the group consisting of chitosen, microcrystalline cellulose, xanthan, HPMC, HPC, HEC, galaotomannons and combinations thereof.

19. The suspension of claim 17, further comprising an effective amount of at least a second active agent selected from the group consisting of analgesics, decongestants, expectorants, anti-tussives, antipyretics, anti-inflammatory agents, cough suppressants and antihistamines.

20. The suspension of claim 19, wherein the second active agent is selected from the group consisting of non-steroidal anti-inflammatory drugs (NSAIDS), propionic acid derivatives, ibuprofen, naproxen, ketoprofen, flurbiprofen, fenoprofen, suprofen, fluprofen, fenbufen; acetic acid derivatives, tolmetin sodium, zomepirac, sulindac, indomethacin, fenamic acid derivatives, mefenamic acid meclofenamate sodium, biphenyl carboxylic acid derivatives, diflunisal, flufenisal, oxicams, piroxicam, sudoxicam, isoxicam, chlorpheniramine, brompheniramine; dexchlorpheniramine, dexbrompheniramine, triprolidine, chlorcyclizine, diphenhydramine, doxylamine, tripelenamine, cyproheptatine, bromodiphenhydramine, phenindamine, pyrilamine, azatadine, acrivastine, astemizole, azelastine, cetirizine, ebastine, fexofenadine, ketotifen, carbinoxamine, desloratadine, loratadine, pheniramine, thonzylamine, mizolastine, terfenadine, chlophendianol, caramiphen, dextromethorphan, diphenhydramine, codeine, hydrocodone, pseudoephedrine, ephedrine, phenylephrine, phenylpropenolamine, terpin hydrate, guaifenesin, potassium, potassium guaicolsulfonate, Cox 2 inhibitors, Celecoxib, Rofecoxib, Valdecoxib, aspirin, acetaminophen, phenacetin, salicylate salts and combination thereof.

21. The suspension of claim 20, wherein the second active agent is selected from the group consisting of chlorpheniramine, dextromethorphan, guaifenesin, acetaminophen, chlorphendianol, doxylamine succinate and ibuprofen.

* * * * *